(12) United States Patent  
Soltani

(10) Patent No.: US 10,151,879 B2  
(45) Date of Patent: Dec. 11, 2018

(54) PHOTONIC DEVICE FOR ULTRAVIOLET AND VISIBLE WAVELENGTH RANGE

(71) Applicant: Raytheon BBN Technologies Corporation, Cambridge, MA (US)

(72) Inventor: Mohammad Soltani, Belmont, MA (US)

(73) Assignee: Raytheon BBN Technologies Corporation, Cambridge, MA (US)

( * ) Notice: Subject to any disclaimer, the term of this patent is extended or adjusted under 35 U.S.C. 154(b) by 0 days.

(21) Appl. No.: 15/468,583

(22) Filed: Mar. 24, 2017

(65) Prior Publication Data

US 2017/0336562 A1    Nov. 23, 2017

Related U.S. Application Data

(60) Provisional application No. 62/338,650, filed on May 19, 2016.

(51) Int. Cl.

| | |
|---|---|
| *G02B 6/122* | (2006.01) |
| *G01N 21/77* | (2006.01) |
| *G02B 6/10* | (2006.01) |
| *G02B 6/136* | (2006.01) |
| *G01N 21/03* | (2006.01) |
| *G01N 21/59* | (2006.01) |
| *G02B 6/132* | (2006.01) |

(Continued)

(52) U.S. Cl.  
CPC .......... *G02B 6/122* (2013.01); *G01N 21/0303* (2013.01); *G01N 21/59* (2013.01); *G01N 21/7746* (2013.01); *G02B 6/102* (2013.01); *G02B 6/1223* (2013.01); *G02B 6/132* (2013.01); *G02B 6/136* (2013.01); *G02B 6/29338* (2013.01); *G01N 2201/0873* (2013.01); *G02B 2006/12038* (2013.01); *G02B 2006/12133* (2013.01); *G02B 2006/12135* (2013.01); *G02B 2006/12138* (2013.01)

(58) Field of Classification Search  
None  
See application file for complete search history.

(56) References Cited

U.S. PATENT DOCUMENTS 5,961,924 A * 10/1999 Reichert .............. G01N 21/648  
385/12  
6,657,723 B2    12/2003 Cohen et al.  
(Continued)

OTHER PUBLICATIONS

Soltani et al., "AlGaN/AlN Integrated Photonics Platform for the Ultraviolet and Visible Spectral Range;" Research Article from Optics Express 25415, vol. 24, No. 22; Oct. 31, 2016; 9 Pages.

(Continued)

*Primary Examiner* — Sung H Pak  
(74) *Attorney, Agent, or Firm* — Daly, Crowley, Mofford & Durkee, LLP

(57) ABSTRACT

In one aspect, a photonic device includes a substrate layer comprising magnesium fluoride and an optical guiding layer disposed on the substrate layer. The optical guide layer includes silicon dioxide. The substrate layer and the optical guide layer are transparent at an ultraviolet and visible wavelength range. In another aspect, a method includes oxidizing silicon to form a silicon dioxide layer, bonding the silicon dioxide layer to magnesium fluoride, removing the silicon and performing lithography and etching of the silicon dioxide to form a photonic device.

14 Claims, 5 Drawing Sheets

(51) Int. Cl.
G02B 6/293 (2006.01)
G02B 6/12 (2006.01)

(56) References Cited

U.S. PATENT DOCUMENTS

| | | |
|---|---|---|
| 2007/0223859 A1 | 9/2007 | Kornilovich et al. |
| 2007/0237460 A1* | 10/2007 | Fan .................. G01N 21/7746 385/39 |
| 2009/0245296 A1 | 10/2009 | Santori et al. |
| 2010/0295083 A1 | 11/2010 | Celler |
| 2013/0005605 A1 | 1/2013 | Chakravarty et al. |

OTHER PUBLICATIONS

PCT International Search Report and Written Opinion dated Jul. 6, 2017 for International Application No. PCT/US2017/030743; 14 Pages.

Elmlinger et al., "Comparison of Fabrication Methods for Microstructured Deep UV Multimode Waveguides Based on Fused Silica;" Proc. of SPIE, vol. 9888; Micro-Optics, 2016.

* cited by examiner

PHOTONIC DEVICE FOR ULTRAVIOLET AND VISIBLE WAVELENGTH RANGE

RELATED APPLICATIONS

This application claims priority to Provisional Application Ser. No. 62/338,650 filed on May 19, 2016 and entitled "INTEGRATED PHOTONIC MATERIAL PLATFORM FOR THE UV VISIBLE WAVELENGTH," which is incorporated herein by reference in its entirety.

BACKGROUND

Integrated photonics has the advantage of miniaturization and large scale manufacturing of photonic functionalities for variety of applications. A range of applications are in the ultraviolet and visible (UV-vis) wavelength range. Examples of applications include integrated spectrometers, Raman spectroscopy, chemical/biological sensing, strong and non-linear light-matter interaction at short wavelengths. Many current optical sensing platforms in the UV-vis range exploit table-top and bulky optical devices. As a result, such sensing platforms are not handheld and are mostly used in the labs. Many of the mature and existing integrated photonic platforms operate at infrared or near-infrared for application mostly in data interconnect and communications. Examples include Silicon Photonics and Indium Phosphide Photonics that are used for applications at 1550 nm, but cannot operate at UV-vis wavelengths. There are integrated photonic materials such as silicon nitride that can operate in the visible range; however, when going to shorter wavelength and in the UV range, these integrated photonic materials suffer from strong optical absorption.

SUMMARY

Described herein is a new photonic material platform where the optical guiding layer is made of silicon dioxide and the underneath substrate layer is magnesium fluoride. Both materials have extremely high optical qualities over the entire UV and visible range. The refractive index difference between silicon dioxide and magnesium fluoride is large enough to provide optical waveguiding condition in the UV-vis range, and yet small enough (~0.08-0.1) to avoid extra-small waveguide dimensions at short wavelengths. Single-mode waveguides with sub-micron or micron scale dimensions can be designed and these dimensions are well within the capabilities of lithography and microfabrication technology. Silicon dioxide is a very mature material in microelectronics and photonics and many of existing technologies can be borrowed to implement such silicon dioxide-on-magnesium fluoride photonic devices.

Also, described herein are techniques to fabricate silicon dioxide-on-magnesium fluoride wafers which are used to make photonic devices on this platform.

In one aspect, a photonic device includes a substrate layer comprising magnesium fluoride and an optical guiding layer disposed on the substrate layer. The optical guide layer includes silicon dioxide. The substrate layer and the optical guide layer are transparent at an ultraviolet and visible wavelength range.

In another aspect, a method includes oxidizing silicon to form a silicon dioxide layer, bonding the silicon dioxide layer to magnesium fluoride, removing the silicon and performing lithography and etching of the silicon dioxide to form a photonic device.

DETAILED DESCRIPTION

Described herein are methods to implement an integrated photonic material platform and devices functional in the ultraviolet (UV) and visible wavelength range (e.g., wavelengths as short as 200 nm to wavelengths as long as 800 nm). In one example, a photonic device may include at least one of a waveguide or a resonator. In other examples, the photonic device may include at least one of a directional coupler, a beam splitter, a Mach-Zehnder interferometer, a grating device, and so forth.

Figure 1:
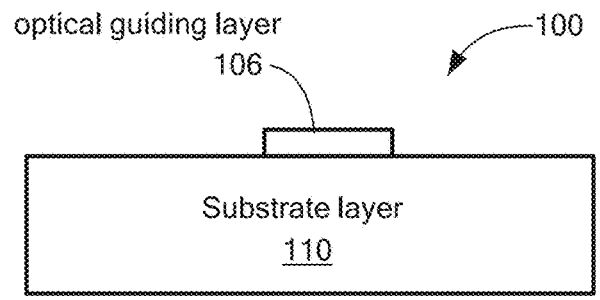
FIG. 1 is a cross-sectional diagram of an example of a photonic waveguiding platform.

Referring to FIG. 1, a photonic platform 100 operating in the UV-visible wavelength range includes an optical guiding layer 106 and a substrate layer 110. The optical guiding layer material 106 is made of silicon dioxide that has a refractive index larger than the underneath substrate 110 which is crystalline magnesium fluoride. The difference between the refractive index of the optical guiding layer 106 and the refractive index of the substrate layer 110 is within ~0.08-0.1. The optical guiding layer 106 and the substrate layer 110 are transparent with negligible or small optical absorption at the UV-visible wavelength range (e.g. less than <0.1 dB/m at a wavelength of 350 nm). The optical guiding layer 106 and the substrate layer 110 are compatible with respect to each other to allow fabrication. In one example, overcladding material (e.g., surrounding at least a portion of the platform 100) can be air or a material like water that has a refractive index less than that of silicon dioxide and is transparent in UV and visible with very small optical absorption.

Figure 2A:
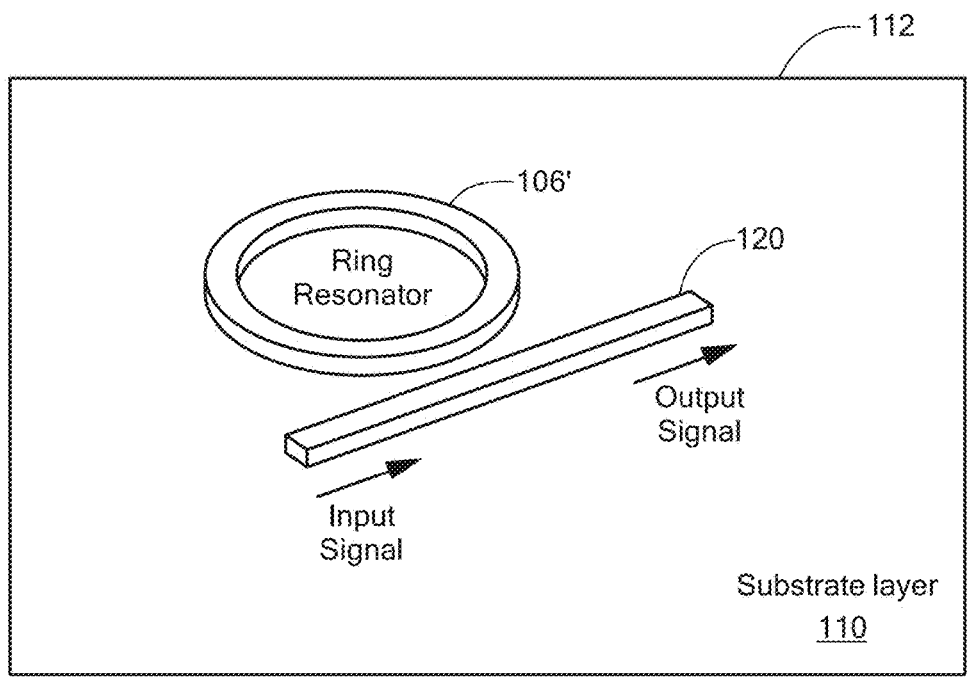
FIG. 2A is a diagram of an example of a photonic device that includes a ring resonator and a waveguide.
Figure 2B:
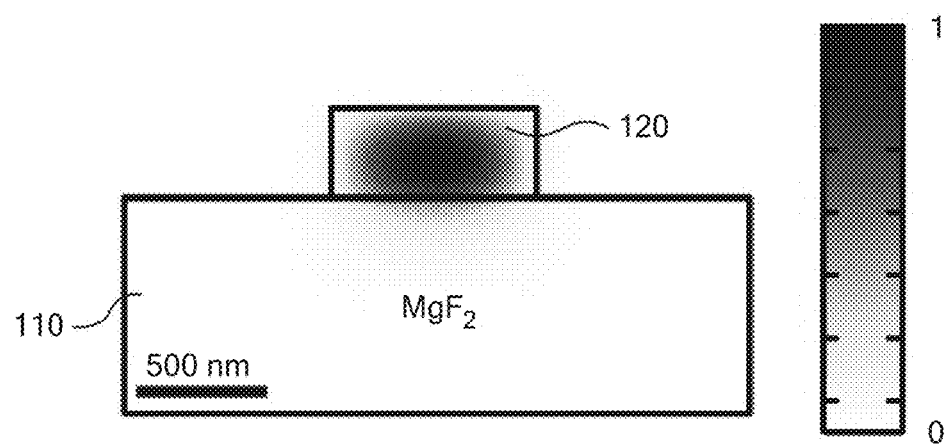
FIG. 2B is a diagram of an example of a simulation of the cross-sectional optical mode profile (electric field distribution) for a silicon dioxide-on-magnesium fluoride waveguide.
Figure 2C:
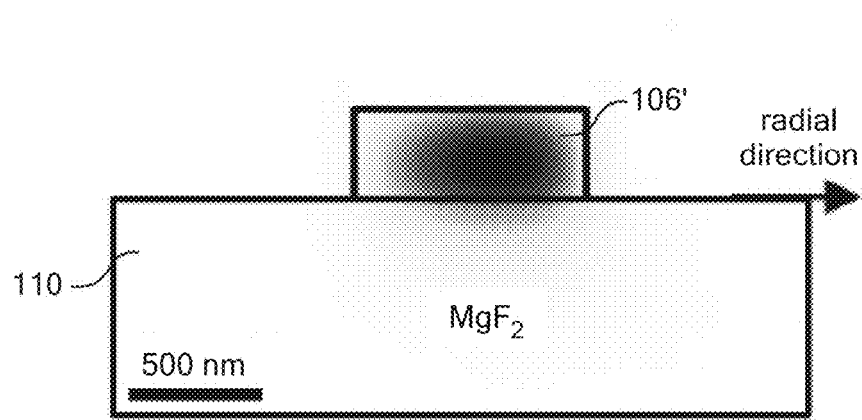
FIG. 2C is a diagram of an example of a cross-sectional optical mode profile for a silicon dioxide-on-magnesium fluoride ring resonator.

Referring to FIG. 2A, an example of a photonic device is a photonic device 112 using the photonic platform 100. The photonic device 112 includes a photonic ring resonator 106' (i.e., an optical guiding layer 106) that includes silicon dioxide, on the substrate layer 110 that includes magnesium fluoride. The photonic device 112 also includes a silicon dioxide waveguide 120 on the substrate layer 110. In this configuration, the ring resonator 106' is side-coupled to the waveguide 120 in order to excite the ring resonator 106'. In one particular example, as shown in FIG. 2B, the silicon dioxide waveguide 120 has a cross sectional dimension of 800 nm×350 nm at a wavelength of 350 nm. In one particular example, as shown in FIG. 2C the ring resonator 106' has a radius of 35 microns and a resonance at about a 350-nm wavelength.

Figure 3A:
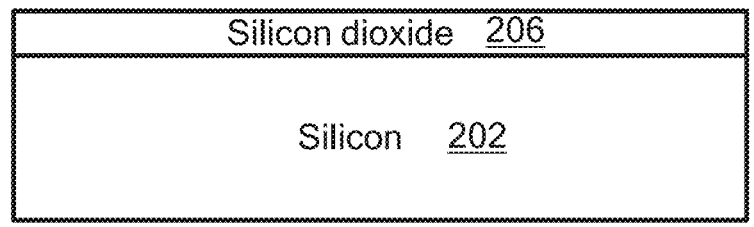
FIGS. 3A to 3E are cross-sectional diagrams to fabricate a silicon dioxide-on-magnesium fluoride photonic device.
Figure 3B:
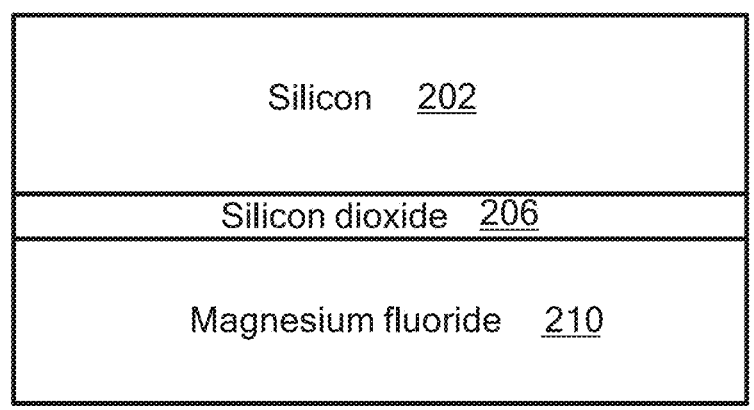
Figure 3C:
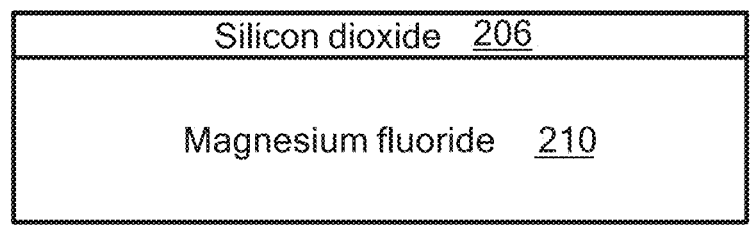
Figure 3D:
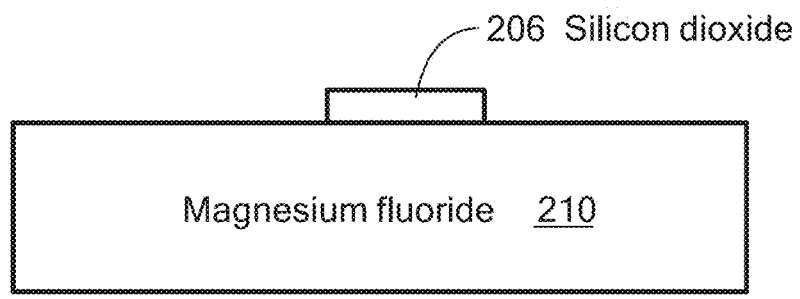
Figure 3E:
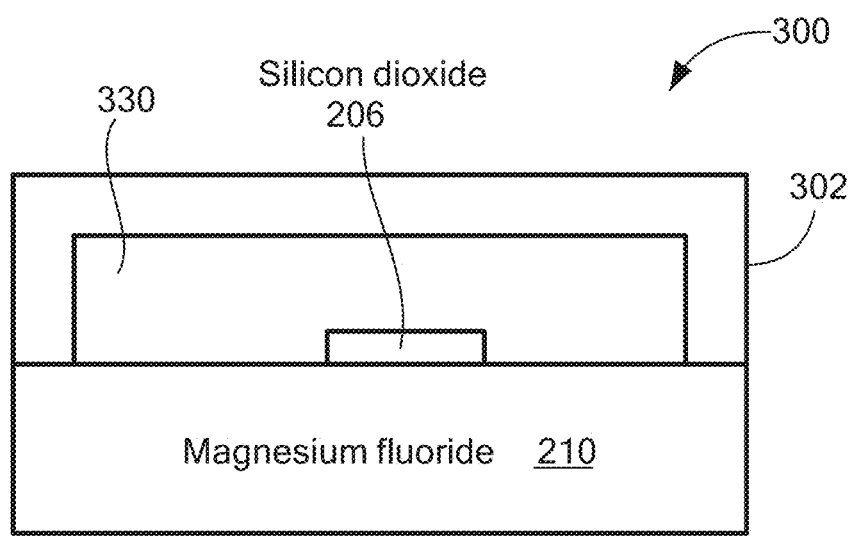

Referring to FIG. 3A to 3E, a photonic device (e.g., a photonic device 300 (FIG. 3E)) may be fabricated to include silicon dioxide and magnesium fluoride. Silicon 202 (e.g., in wafer form) is oxidized to form the silicon dioxide 206 (FIG. 3A). Magnesium fluoride 210 (e.g., in wafer form) is bonded to the silicon dioxide 206 (FIG. 3B). In one particular example, the magnesium fluoride 210 may also include a thin layer of deposited silicon dioxide that is then bonded to the silicon dioxide 206 on the silicon 202. The silicon 202 is removed (FIG. 3C) and the silicon dioxide-on-magnesium fluoride wafer is formed.

Using lithography and etching techniques, for example, which are conventional in microfabrication technology, the silicon dioxide layer 206 is patterned and etched (FIG. 3D) to form the photonics devices in this platform. In one example, lithography and etching may be used to form at least one of a waveguide, a ring resonator, a disk resonator, a directional coupler, a Mach-Zehnder interferometer, a multiplexor, a demultiplexor, an array waveguide grating device, a beam splitter or a grating and periodic device.

Polydimethylsiloxane (PDMS) material 302 is added on portions of the magnesium fluoride 210 to form a fluidic channel 330 (FIG. 3E) that carries fluid such as water or air, for example. In one example, the photonic device 300 may be used in aqueous environments for chemical or biological sensing applications and water monitoring. In other examples, the photonic device 300 can be used to enhance the Raman sensing of chemical/biological material in aqueous environments. In another example, more complicated photonic devices such as spectrometers or optical spectrum analyzer operating at the UV or visible wavelength can be implemented on this platform with a very compact and chip-scale size.

In one example, a metal microheater may be integrated with the photonic device to tune the optical properties using a thermo-optic effect.

Figure 4:
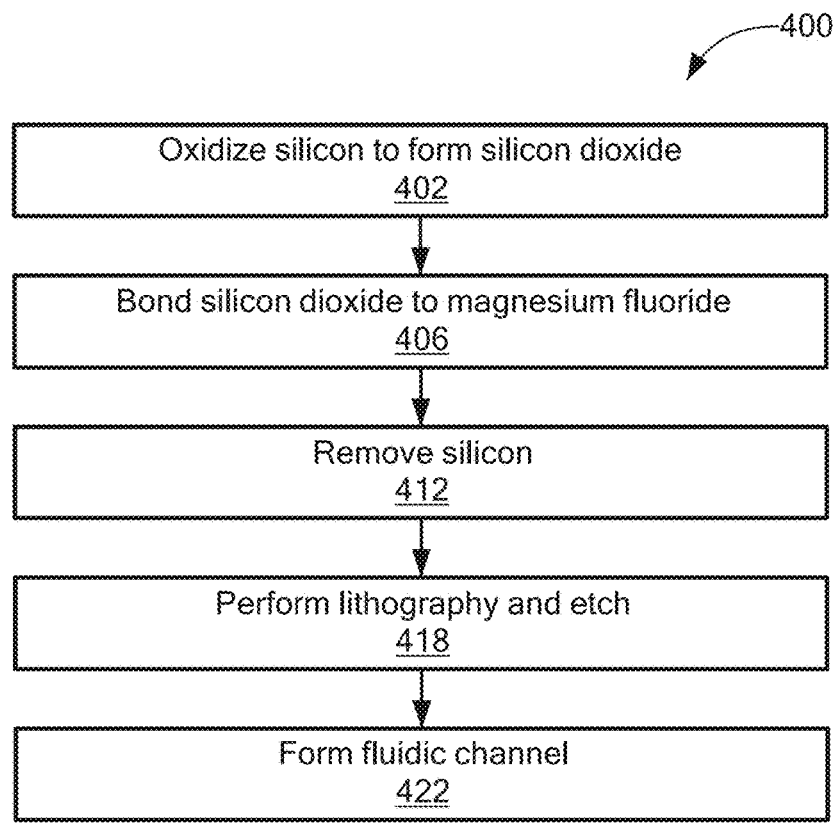
FIG. 4 is a flow diagram of an example of a process to fabricate a silicon dioxide-on-magnesium fluoride photonic device.

Referring to FIG. 4, an example of a process to form a photonic device on silicon dioxide-on-magnesium fluoride platform is a process 400. Process 400 oxidizes silicon to form silicon dioxide (402). In one example, the silicon dioxide 206 is formed using thermal oxidation on silicon 202 (e.g., silicon wafer) (see, for example, FIG. 3A).

Process 400 bonds the silicon dioxide to a magnesium fluoride. In one example, silicon dioxide 206 is bonded to magnesium fluoride 210 (see, for example, FIG. 3B). In one particular example, the magnesium fluoride 210 includes a layer of deposited silicon dioxide (e.g., 10-50 nm) (not shown) that was deposited using atomic layer deposition or plasma enhanced chemical vapor deposition, for example and the silicon dioxide 206 is bonded to the silicon dioxide on the magnesium fluoride.

Process 400 removes the silicon (412). For example, the silicon may be removed using plasma etching or wet etching using KOH chemical, or a combination of plasma and wet etching.

Process 400 performs lithography and etch (418). In one example, the lithography and etching process shapes the silicon dioxide to form a ring resonator.

Process 400 forms a fluidic channel. In one example, the PDMS material 302 is deposited on at least a portion of the magnesium fluoride 210 and over the silicon dioxide to form the fluidic channel 330 (see, for example, FIG. 3E).

Figure 5:
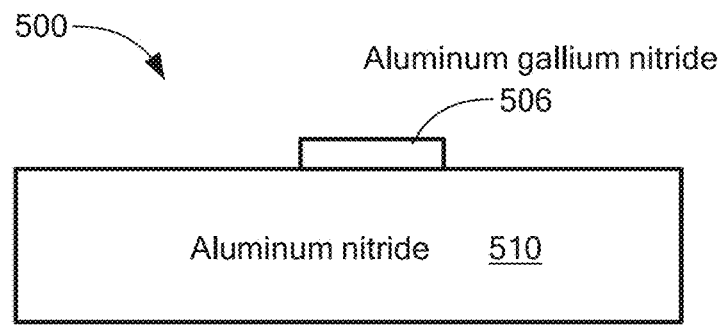
FIG. 5 is a cross-sectional diagram of another particular example of the photonic platform of FIG. 1.

Referring to FIG. 5, another particular example of a photonic platform 100 is a photonic platform 500. The photonic platform 500 includes aluminum gallium nitride (AlGaN) 506 as a light guiding layer and aluminum nitride (AlN) 510 as the adjacent material. In one example, the operational wavelength of the photonic platform 500 is greater than 260 nm.

The processes described herein are not limited to the specific examples described. For example, the process 400 is not limited to the specific processing order of FIG. 4. Rather, any of the processing blocks of FIG. 4 may be re-ordered, combined or removed, performed in parallel or in serial, as necessary, to achieve the results set forth above.

The processes described herein are not limited to the specific embodiments described. Elements of different embodiments described herein may be combined to form other embodiments not specifically set forth above. Other embodiments not specifically described herein are also within the scope of the following claims.

What is claimed is:

1. A planar integrated photonic device with single and highly confined optical mode comprising:
    a substrate layer comprising magnesium fluoride in crystalline wafer form; and
    an optical guiding layer disposed on the substrate layer and comprising silicon dioxide in wafer form, the silicon dioxide formed by oxidizing silicon and the optical guiding layer is bonded to the substrate layer with a thin layer of deposited silicon dioxide,
    wherein the substrate layer and the optical guide layer are transparent at an ultraviolet and visible wavelength range.

2. The planar integrated photonic device of claim 1, wherein the optical guiding layer is a ring resonator.

3. The planar integrated photonic device of claim 1, further comprising a waveguide and a ring resonator disposed on the substrate layer.

4. The planar integrated photonic device of claim 1, further comprising a material in contact with the substrate layer forming a fluidic channel.

5. The planar integrated photonic device of claim 4, wherein the fluidic channel contains water.

6. The planar integrated device of claim 4, wherein the fluidic channel contains a biochemical liquid.

7. The planar integrated photonic device of claim 6, wherein the photonic device is one of a chemical or biological sensor.

8. A method to fabricate a silicon dioxide-on-magnesium fluoride single mode photonic device, comprising:
    oxidizing silicon in wafer form to form a silicon dioxide layer;
    bonding the silicon dioxide layer to a layer of magnesium fluoride in crystalline wafer form, the layer of magnesium fluoride including a thin layer of deposited silicon dioxide that is bonded to the silicon dioxide layer;
    removing the silicon; and
    performing lithography and etching of the silicon dioxide to form a single mode photonic device.

9. The method of claim 8, further comprising depositing polydimethylsiloxane (PDMS) on at least a portion of the layer of magnesium fluoride to form a fluidic channel.

10. The method of claim 9, further comprising placing water in the fluidic channel.

11. The method of claim 9, further comprising placing a biochemical liquid in the fluidic channel.

12. The method of claim 8, wherein performing lithography and etching of the silicon dioxide comprises performing lithography and etching of the silicon dioxide to form at least one of a wave guide, a ring resonator, a disk resonator, a directional coupler, a Mach-Zehnder interferometer, a multiplexor, a demultiplexor, an array waveguide grating device, a beam splitter or a grating and periodic device.

13. The method of claim 8, wherein performing lithography and etching of the silicon dioxide comprises performing lithography and etching of the silicon dioxide to form a single mode waveguide.

14. The method of claim 8, further comprising integrating a metal microheater with the single mode photonic device to tune the optical properties using a thermo-optic effect.

* * * * *